United States Patent
Weber et al.

Patent No.: US 6,482,234 B1
Date of Patent: Nov. 19, 2002

(54) PROSTHETIC SPINAL DISC

(75) Inventors: Paul J. Weber, Ft. Lauderdale, FL (US); Luiz B. Da Silva, Danville, CA (US)

(73) Assignee: Pearl Technology Holdings, LLC, Tampa, FL (US)

(*) Notice: Subject to any disclaimer, the term of this patent is extended or adjusted under 35 U.S.C. 154(b) by 0 days.

(21) Appl. No.: 09/558,896

(22) Filed: Apr. 26, 2000

(51) Int. Cl.[7] .................................................. A61F 2/44
(52) U.S. Cl. ............................... 623/17.12; 623/17.13; 623/17.16
(58) Field of Search ........................... 623/17.12, 17.13, 623/17.15, 17.16, 17.11

(56) References Cited

U.S. PATENT DOCUMENTS

| | | | | |
|---|---|---|---|---|
| 3,875,595 A | * | 4/1975 | Froning | 623/17.11 |
| 4,863,477 A | * | 9/1989 | Monson | 623/17.11 |
| 4,932,969 A | * | 6/1990 | Frey | 623/17.11 |
| 5,035,716 A | * | 7/1991 | Downey | 623/17.11 |
| 5,047,055 A | * | 9/1991 | Bao | 623/17.11 |
| 5,123,926 A | * | 6/1992 | Pisharodi | 623/17.11 |
| 5,171,280 A | * | 12/1992 | Baumgartner | 623/17.11 |
| 5,192,326 A | * | 3/1993 | Bao | 623/17.11 |
| 5,571,189 A | * | 11/1996 | Kuslich | 623/17.12 |
| 5,755,797 A | * | 5/1998 | Baumgartner | 623/17.12 |
| 6,187,043 B1 | * | 2/2001 | Ledergerber | 623/17.12 |

* cited by examiner

Primary Examiner—David H. Willse
Assistant Examiner—Cheryl L Miller
(74) Attorney, Agent, or Firm—John P. Wooldridge

(57) ABSTRACT

A prosthetic spinal disc may include a nucleus and an annulus that together may be optionally shaped, using a computed tomography (CT) scan, ultrasound imaging and/or magnetic resonance imaging (MRI). The nucleus includes a central area having a material density that is different than the material density of the annulus. The nucleus may alternately include an area for the introduction of a central supporting fluid or gel. An optional fiberoptic carriage may be used to provide tissue ingrowth from the supported vertebrae and optional internal baffling provides additional stabilization.

18 Claims, 3 Drawing Sheets

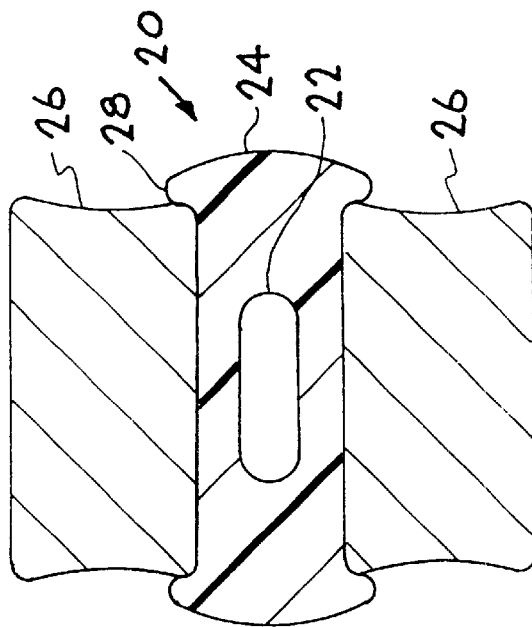
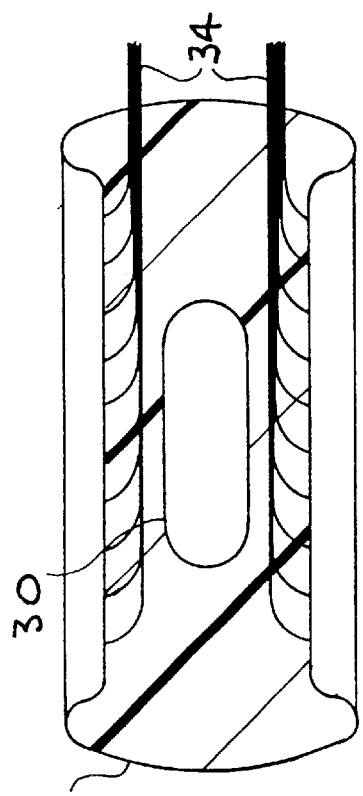
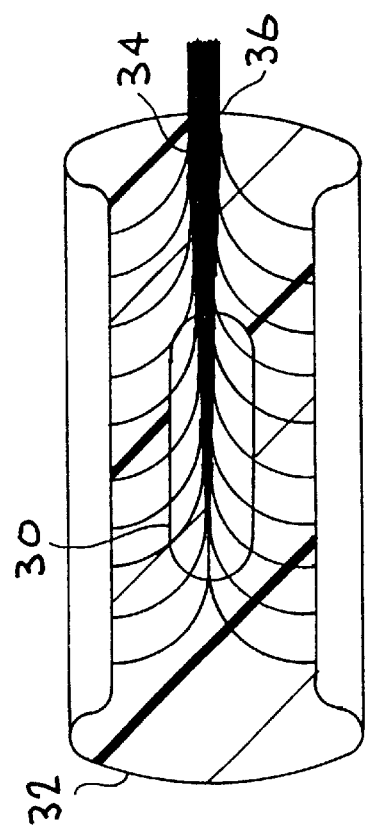
FIG. 1 (PRIOR ART)
FIG. 2
FIG. 3A
FIG. 3B

PROSTHETIC SPINAL DISC

BACKGROUND OF THE INVENTION

1. Field of the Invention

The present invention relates to a posthetic spinal annulus to be used in combination with a disc nucleus and more specifically, it relates to a surgically implantable intradiscal prosthesis and the method of manufacture thereof.

2. Description of Related Art

The vertebral spine is a complex arrangement of many structures, with many facets (areas of specially cushioned apposition). The vertebral bones are twenty-four in number, not including the sacrum, and they gradually vary in size and shape and load distribution from the cervical to the thoracic to the lower lumbar vertebrae. The vertebrae, amazingly, are very different between the first cervical and the last lumbar vertebra. Nonetheless, as shown in FIG. 1, the bony vertebral bodies 10 of the spine are each separated by a relatively soft intervertebral disc 12, which acts as a joint, allowing flexion, extension, lateral bending, and axial rotation. Fibrous tissues, emulating scar tissues, may act somewhat similarly to the bonding elements that make up the ligaments of the spine, as well as the outer portions of the relatively soft intervertebral discs. If a synthetic vertebral disc were to be placed to repair one that is naturally damaged, it would be beneficial to have the participation of these fibrous fixing elements in a relatively controlled and maximized fashion.

The typical vertebra has a thick interiorly located bone mass called the vertebral body (with a neural vertebral arch that arises near the posterior surface of the vertebral body). The intervertebral disc primarily serves as a mechanical cushion between the vertebral bones, permitting controlled motion within the vertebral segments of the axial skeleton. The normal disc is a unique mixed structure, comprised of three component tissues, including the nucleus pulposis (nucleus), the annulus fibrosus (annulus), and the two opposing vertebral end plates. The two vertebral end plates are each composed of thin cartilage overlying a thin layer of hard cortical bone, which attaches to a spongy, richly vascular cancellous bone of the vertebral body. The vertebral end plates thus serve to attach the adjacent vertebra to the disc. In other words, a transition zone is created by the end plates between the malleable disc and the bony vertebra.

The annulus of the disc is a tough outer fibrous ring that binds together the adjacent vertebrae. The fibrous portion is much like a laminated automobile tire measuring about 10 to 15 mm in height and about 15 to 20 mm in thickness. Fibers of the annulus consist of 15 to 20 overlapping multiple plies and are attached at the superior and inferior vertebral body at a roughly 30-degree angle in both directions. This configuration particularly resists torsion as about half of the angulated fibers will tighten when the vertebrae rotate in either direction relative to each other.

Inside the annulus there is a relatively liquid core, the nucleus. The healthy natural nucleus has a high water content and aids in the load bearing and cushioning properties of the spinal disc; however, the spinal disc may be displaced or damaged due to trauma or disease. A disc herniation occurs when the annulus fibers are weakened or torn and the nucleus becomes permanently stressed, extended, or extruded out of its normal internal annular confines. A herniated or slipped nucleus can compress a spinal nerve posteriorly, resulting in pain, loss of muscle control, or even paralysis. Alternatively, in disc degeneration the nucleus loses its water binding capacity and deflates as though the air had been let out of a tire. Subsequently, height of the nucleus decreases, causing the annulus to buckle in areas where the laminated plies are loosely bonded. As the overlapping laminated plies of the annulus begin to buckle and separate, either circumferential or radial annular tares may occur and contribute to persistent and disabling pain. Adjacent ancillary spinal facet joints to the rear may also be forced into an overriding position, which may cause additional back pain as tissues are damaged due to irregular contact and force application.

SUMMARY OF THE INVENTION

It is an object of the present invention to provide a prosthetic spinal disc made of biocompatible material and having a nucleus with a material density that is different from the material density of the disc annulus.

It is another object of the invention to provide a prosthetic spinal disc that includes materials that vary in density.

It is another object of the invention to provide a prosthetic spinal disc including a nucleus and an annulus that may be optionally shaped, using a computed tomography (CT) scan, ultrasound imaging and/or magnetic resonance imaging (MRI) where the nucleus provides a central open reception area for the introduction of a central supporting fluid or gel.

Still another object of the present invention is to provide a prosthetic spinal disc having an optional fiber optic carriage that is used to transmit wavelengths of light which will stimulate tissue ingrowth from the supported vertebrae.

Another object of the invention is to provide a prosthetic spinal disc including an annulus and a nucleus having internal baffling to provide additional stabilization.

The invention-is a prosthetic spinal disc including a nucleus and an annulus that may be optionally shaped, using a computed tomography (CT) scan, ultrasound imaging and/or magnetic resonance imaging (MRI). The nucleus provides a central open reception area for the introduction of a central supporting fluid or gel. An optional fiber optic carriage or alternatively hollow continuous porosities is used to provide tissue ingrowth from the supported vertebrae and optional internal baffling provides additional stabilization.

The use of computed tomography (CT), ultrasound imaging and/or magnetic resonance imaging (MRI) enables the use of the bony irregularities of the vertebrae to create a tight fit for the spinal disc. The present invention provides stereotactic forming, either manually or automated, using a CAT scanner, MRI or three-dimensional ultrasound in order to shape a prosthetic spinal disc. This will simulate the outer portion of the natural disc (annulus). An overlapping contoured lip protrudes from the edge of the prosthetic annulus to cap and contain the movement of the vertebrae above and below the prosthetic spinal disc.

An alternative aspect of the invention utilizes certain wavelengths of laser light to cause ingrowth of beneficial tissues and cells. Electromagnetic energy may be transported through fiber optics to portions of the vertebral disc for extended periods of time, using the disc as an actual carrying mechanism. Ingrowth of fibrocartilagenous tissues into porosities may be generated to lock the disc in place.

The prosthetic nucleus and annulus of the present invention may be formed as an integral unit, where the fiber optics pass through the nucleus and then into the annulus. Alternately, the fiber optics may only pass through the annulus portion. Internal baffles may divide portions of the annulus, which provides a central open nuclear reception area for the introduction of a central supporting fluid or gel.

Baffles or septae serve to restrain the movement and reduce shock to portions of the prosthetic annulus.

A further variant of this disc contains a silicone or relatively gelatinous polymer in the nucleus that simulates the nucleus of the natural disc. Additionally, the implant may contain a rigid lip around the edge in order to help hold it in place between the superior and inferior vertebral bodies. It may be desirable that the external few millimeters of the vertebra and disc be porous. The lip may also include porosities. The porosities may be relatively oriented in a circular pattern in order to mimic the natural positioning of the elements that hold on to the disc from the bony elements. Additionally, growth factors or living cells may be incorporated into the polymer surrounding the holes in order to aid cell growth.

BRIEF DESCRIPTION OF THE DRAWINGS

FIG. 1 shows the bony vertebral bodies of the spine separated by a relatively soft intervertebral disc.

FIG. 2 is a prosthetic spinal disc, including a nucleus and an annulus and showing the overlapping contoured lip.

FIG. 3A is a prosthetic spinal disc, including a nucleus and an annulus and a fiber optic carriage that passes through the nucleus material to provide tissue ingrowth.

FIG. 3B is a view where the fiber optic passes through the annulus.

DETAILED DESCRIPTION OF THE INVENTION

Figure 4:
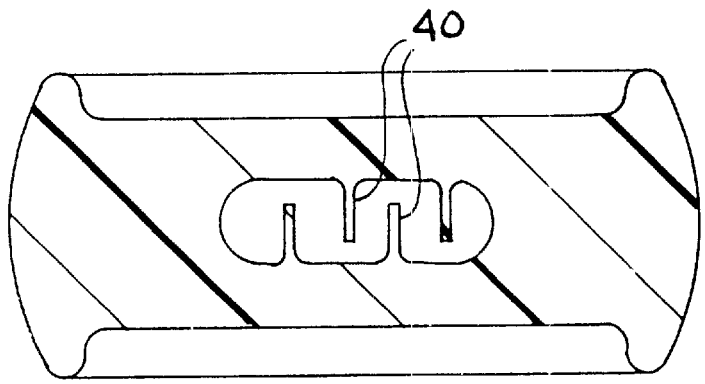
FIG. 4 shows a prosthetic spinal disc, including a nucleus and an annulus and internal baffling or septae.

The invention is a prosthetic spinal disc 20 as shown in FIG. 2 and includes a nucleus 22 and an annulus 24 that together may be optionally shaped, using a computed tomography (CT) scan, ultrasound imaging and/or magnetic resonance imaging (MRI). The nucleus and/or the annulus may be made of biocompatible material. The nucleus provides a central open reception area for the introduction of a central supporting fluid or gel. An optional fiberoptic carriage may aid tissue ingrowth from the supported vertebra 26 and optional internal baffling provides additional stabilization.

Although detailed embodiments of the present invention are disclosed, these embodiments are merely exemplary of the present invention. It is to be understood that the present invention may be embodied in various systems and the specific details disclosed herein are not to be interpreted as limiting, but rather as a basis for the claims and as a representative basis for teaching one skilled in the art to variously practice the present invention.

In the present invention, the use of computed tomography (CT), ultrasound imaging and/or magnetic resonance imaging (MRI) enables the use of the bony irregularities of the vertebrae to create a tight fit for the spinal disc. When soft doughnut-like discs degenerate in between the bony vertebrae above and below, there are usually other problems with the plates and, therefore, the shapes of the vertebrae above and below are abnormally shaped. The plates usually become spurred, burred, and curved and are not very flat unless the surgeon sands them down. Thus, the present invention provides stereotactic forming, either manually or automated, using a CAT scanner, MRI or three-dimensional ultrasound in order to shape a prosthetic spinal disc. This will simulate the outer portion of the natural disc (annulus).

The imaging of the vertebrae is used to determine the abutting vertebrae dimensions and their conformations, to which the implant may be contoured either by computer-controlled robotic mechanism or by manual reduction. Additionally, contouring may be planned in the area of the abutting vertebral bony bodies, which may be used in combination with the manual or automated contouring that will take place upon the prosthesis prior to surgery.

The prosthetic manipulation would likely be in a laboratory prior to surgery, and the human body vertebral bony area manipulation would take place at the time of surgery. Either could be computer or manually controlled. Nonetheless, the three-dimensional contouring needs would be assessed and pre-planned by the use of MRI, three-dimensional ultrasound imaging and/or CT imaging.

WO 89/11257, titled "Method And System For Making Prosthetic Device", incorporated herein by reference, is directed to a method of making a prosthetic device or a three-dimensional object having surface characteristics derived from data obtained from a patient and from data created to modify the surface characteristics of the object Such data is obtained by sensing the object by transducer. A solid modeling system with memory and a processor, and process control elements construct three dimension data files based upon mathematical creation of the solid model with cuberille data. Various transducers are illustrated, including free wand transducers of plane image location and xyz coordinate location of subject elements, and a system for sampling data from ultrasound, a CT scan, a Magnetic Resonant Imaging (MRI) scan and other techniques, along with surgical methods of treatment and diagnosis. The information in WO 89/11257 is one example of a method of forming a three dimensional object based on imaging with CT, ultrasound and/or magnetic resonance.

Other methods of fabrication based on three-dimensional imaging techniques are known in the art and are within the scope of the present invention. For example, rapid proto-typing techniques are usable to form the prosthetic disc of the present invention. U.S. Pat. No. 5,303,141, titled "Model Generation System Having Cosed-Loop Extrusion Nozzle Positioning", incorporated herein by reference, describes an apparatus and method for fabricating a three-dimensional object in accordance with a CAD-generated specification of the object U.S. Pat. No. 5,902,537 titled "Rapid Recoating Of Three-Dimensional Objects Formed On A Cross-Sectional Basis 3D Systems, Inc.", incorporated herein by reference, is directed to methods for use in building three-dimensional objects on substantially a cross-sectional basis by forming successive layers using counter-rotating rollers, ink jet recoaters, spinning members which sling material, applicator bars that dispense material via a meniscus and/or independently dispensed streams. U.S. Pat. No. 5,370,692 titled "Rapid, Customized Bone Prosthesis", incorporated herein by reference, describes the fabrication of prosthetic bone implants to approximately replicate a patient's original bone. Medical computer aided imaging techniques are applied to generate a data base representing the size and shape of the original bone in a three dimensional coordinate system. The implantable replica is fabricated using the data base and free form manufacturing to sequentially solidify adjoining, cross-sectional intervals of a fluid material. Appropriate fluid materials include ceramic particles that may be selectively bonded by sintering or bonding with a polymer, and a monomer that is polymerized at selected regions by an incident laser beam. U.S. Pat. No. 5,510,066 titled "Method For Free-Formation Of A Free-Standing, Three-Dimensional Body", incorporated herein by reference, discloses a method for preparing a self-supporting or free-standing three-dimensional unitary structural body by generating successively a plurality of cross-sectional layers of the body, one layer on top of the other and with the layers joined together to form the body and with the generating of a cross-sectional layer by placing a plurality of drops of a liquid composition, containing a first reactant, in a pattern of discrete drops making up the cross-sectional layer and subsequently placing a plurality of discrete drops of other liquid composition, containing another reactant, in contact with the placed drops ion the pattern so that the first reactant and the other reactant react to provide a solid. Other methods for forming the prosthetic disc will be apparent to those skilled in the art, based on the teachings herein.

An overlapping contoured lip 28, shown in FIG. 2, protrudes about 3–7 mm at the edge of the prosthetic annulus 24, depending upon the vertebra in question (3 mm in the cervical region and 5 to 7 mm in the lumbar region of the body), to cap and contain the movement of the vertebrae 26 above and below the prosthetic spinal disc 20. Even though the vertebrae 26 above and below the disc have some ligaments controllably limiting their movements, most of the ligaments usually have become significantly weakened in patients with disc disease, because the vertebrae have already flopped around to some degree for a period of years, stretching, pulling, and tearing the ligaments. Therefore, it is expected that the previous original ligament may not hold as securely as a well-fashioned lip that would exist around the edge of the prosthetic spinal disc and annulus of the present invention. Some ligaments interfering with the proposed discal implantation and affixation may require surgical modification.

Certain wavelengths of laser light (e.g., delivered by fiber optics) can cause ingrowth of beneficial tissues and cells in areas where animals have had their vertebral discs deliberately damaged by scientists. The present invention utilizes electromagnetic (ie. laser or intense pulsed light or intense multispectral light, etc) energy to produce such ingrowth. Electromagnetic energy may be transported through fiber optics to portions of the vertebral disc for extended periods of time, using the disc as an actual carrying mechanism. Ingrowth of fibrocartilagenous tissues into porosities may be generated to lock the disc in place.

The effect of laser radiation on the regeneration processes in spine cartilage has been studied in-vivo by Emil N. Sobol et al. as well as other researchers. Rabbits were used as a model and a Holmium (2.09 $\mu$m ) and an Erbium fiber laser (1.56 $\mu$m) for irradiation of discs that were opened to remove the annulus fibrosis and the nucleus pulposis of the intervertebral disc. The irradiated zone was examined using optical coherent tomography one month after the operation and conventional histological techniques two months after the laser operation. It was observed that laser radiation promotes the growth of the new cartilaginous tissue of fibrous and hyaline types. The lasers used were a pulsed HO:YAG laser at a wavelength of 2.09 $\mu$m, a pulse duration of about 300 $\mu$s, and a pulse repetition rate of 5 Hz. The energy of the laser pulse was varied from 0.005 Joules to 0.08 Joules. Alternately, a continuous wave Erbium fiber laser at a wavelength of 1.56 $\mu$m and a power of from 1.5 to 3.0 watts was used. Alternate electromagnetic radiation generating systems may be substituted for the lasers and the parameters described herein. The use of any wavelength of light at continuous wave and any pulse duration at any intensity that will induce tissue activation is useable in the present invention and falls within the scope thereof.

The prosthetic nucleus and annulus of the present invention may be formed as an integral unit, where the fiber optics pass through the nucleus and then into the annulus. Alternately, the fiber optics may only pass through the annulus portion. FIG. 3A is a prosthetic spinal disc, including a nucleus 30 and an annulus 32. The disc further comprises a fiberoptic carriage 34 having a plurality of fiber optics to provide tissue ingrowth. In this embodiment, the fiberoptic passes through a portion of the annulus 32 and then directly through the material comprising the nucleus 30. The fiber optics are terminated at or near the surface 36 of annulus 32. FIG. 3B shows an alternate embodiment where the fiber optics 34 pass through the annulus 32 without passing through the nucleus 30.

Internal baffles 40, shown in FIG. 4, may divide portions of the annulus, which provides a central open nuclear reception area for the introduction of a central supporting fluid or gel. Baffles or septae 40 serve to restrain the movement and reduce shock to portions of the prosthetic disc. The small internal baffles or septae placed within the area containing the nucleus help maintain the shape and rigidity, as well as to reduce shock for example when a person would be bending forward and creating a force that would force the nucleus material toward the posterior section. Flow and shock may also be reduced by these internal walls or septae because they reduce passage of the fluid to a large degree.

Figure 5:
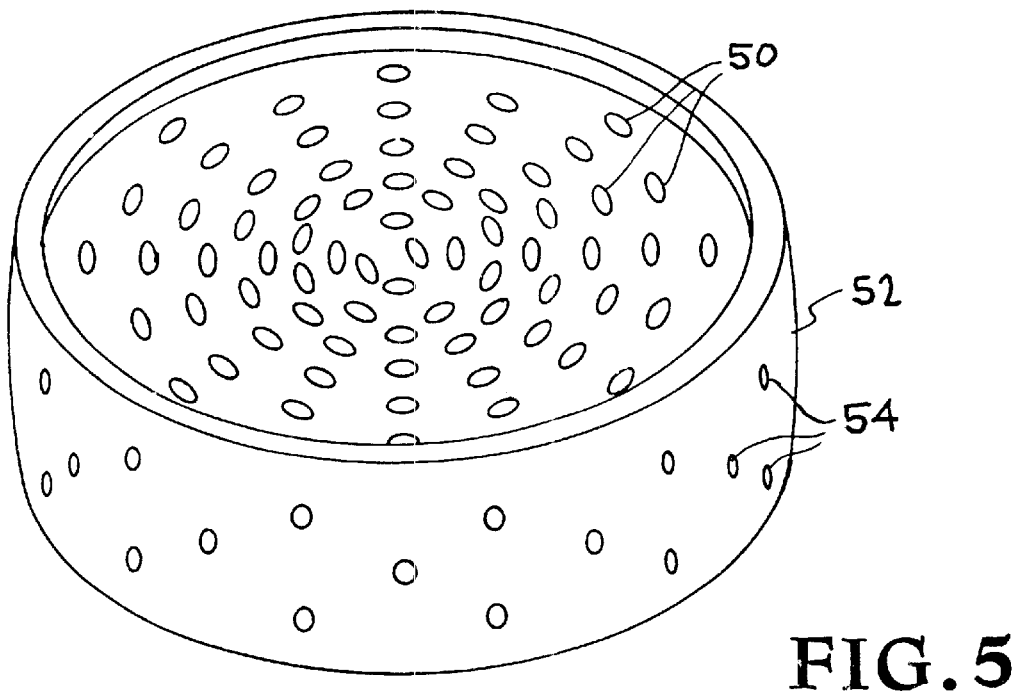
FIG. 5 illustrates the porosity of the external few millimeters of the vertebra and disc.

A further variant of this disc may contains a silicone or relatively gelatinous polymer in the nucleus that simulates the nucleus of the natural disc. Additionally, the implant may contain a rigid lip around the edge in order to help hold it in place between the superior and inferior vertebral bodies. It may be desirable that the external few millimeters of the vertebra and disc be porous as illustrated in FIG. 5. The porosities 50 impinge at angle (e.g., 30 degrees) on the surface of the prosthetic disc, in order to mimic the natural situation. The lip 52 may also include porosities 54. It is advantageous in some cases to provide a porosity that is of a dimension of ½ mm diameter and 5 mm long. The porosity can be laser drilled or fashioned by other mechanisms. It is advantageous that the porosities are relatively oriented in a circular pattern in order to mimic the natural positioning of the elements that hold on to the disc from the bony elements.

Growth factors may be incorporated into the polymer surrounding or within the holes themselves in order to help make cells grow into there. Living cells could also be cultured into those areas, which would grow from the implant into the bone. Another way could be to incorporate cells into the disc and have them grow into the bone.

The fiber optics may be extremely thin (e.g., single mode) in diameter and may number up to hundreds. If there is a highly fluid low viscosity substance mimicking the nucleus, the fiber optics could not pass through the nucleus area without risking a leak. Fiber optics would therefore be restricted in their presence only to areas within the synthetic annulus. Nonetheless, if a highly gelatinous or rubbery material is used to make the nucleus, then this synthetic nucleus material would be less likely to extrude through little holes along the periphery of the disc and the joining of it with the material that composes the synthetic annulus. Under such conditions, the fiberoptic can pass through the nucleus material.

Figure 6:
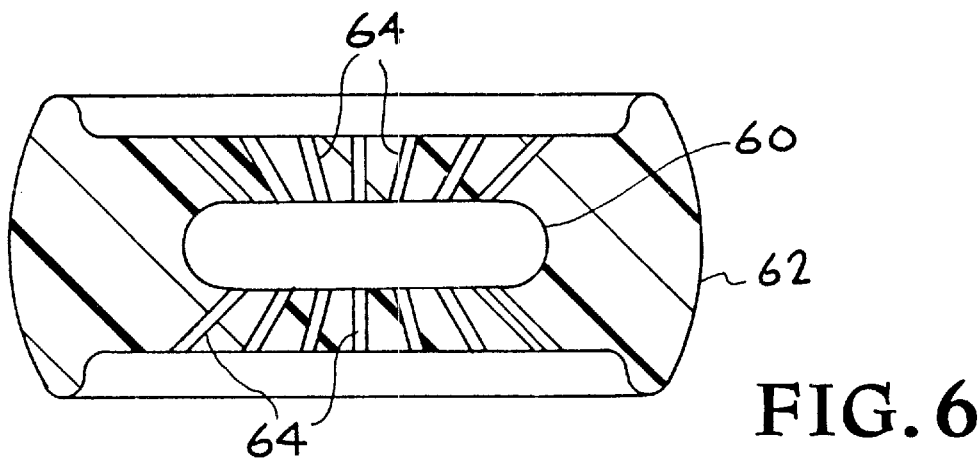
FIG. 6 shows a synthetic bio-compatible nucleus.

The nucleus material does not necessarily have to be biocompatible, if it is "shielded" from the body by the annulus. In such cases, silicone may be used if the spinal disease is serious and other gelatinous polymers that are less noted to create difficulty in humans could not be used. It is usually preferable that the fiber optics enter the disc from the anterior portion, i.e., the portion of the vertebra facing the stomach since it is often that the surgery would be carried out from the "anterior approach," which would mean an incision through the stomach area or the neck area in order to reach the various areas of the spinal column. It would be necessary that all the prostheses be uniquely created, depending upon the areas to be treated. For example, the intervertebral discs in the neck area are often less than 1 cm in thickness, while the area in the lower lumbar spine, needing to accommodate weight and shock, may vary up to 2+ cm in thickness. Nonetheless, other approaches to fiberoptic/ disc attachment may be possible. Examples of biocompatible materials usable in the present invention include polypropylene, polyethylene, polytretrafluoroethylene, polyurethane, and polydimethylsiloxane Alternately, a "bio-synthetic" annulus may be made up of purely natural material such as collagen and fibroblasts that are cultured using biological engineering methods now becoming available. The fiber optics could be placed and pass through here also. However, a synthetic biocompatible nucleus may be needed to provide a small chamber for synthetic nuclear material that would also be biocompatible. The aforementioned material could be attachable to the fibrocartilagenous synthetic material that would be made to surround it The fiberoptic, or inflation ports may also exit the anterior facing direction of the implant in order to facilitate inflation or fiberoptic connection during surgery. Referring to FIG. 6, a prosthetic spinal disc includes a nucleus 60, an annulus 62 and a system of thin canals 64. Which could be empty, filled with growth factors or contain fiber optics.

Figure 7A:
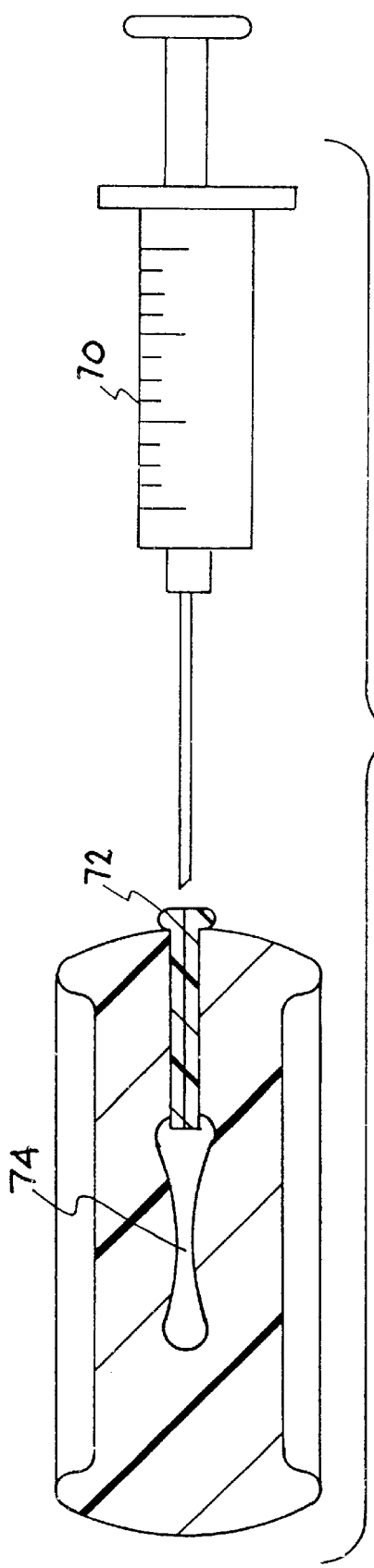
FIGS. 7A and B show the inflation means or valves.
Figure 7B:
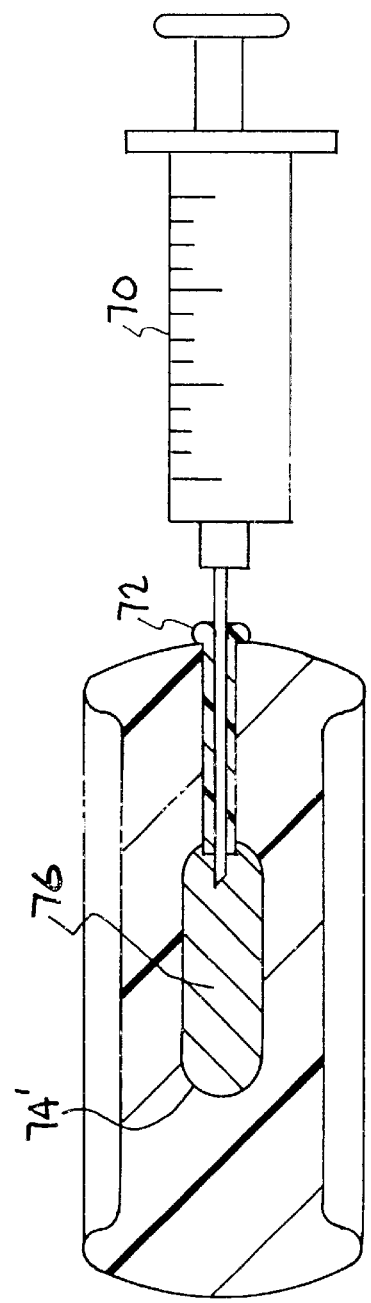

FIGS. 7a and 7B show a means for inflating the nucleus of the present invention. Referring to FIG. 7A, a syringe 70, filled with any of the materials used for inflating the nucleus described above, or other materials as would be apparent to those skilled in art as a result of the description herein, is inserted through a valve 72 such that the syringe needle is located within the collapsed nucleus 74. When the syringe plunger is used to compress the materials within the syringe body, the materials 76 fill and expand the nucleus 74'.

The foregoing description of the invention has been presented for purposes of illustration and description and is not intended to be exhaustive or to limit the invention to the precise form disclosed. Many modifications and variations are possible in light of the above teaching. For example, although the present invention provides for a prosthetic human intervertebral disc, this disc may be used for racehorses and other animals of value. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

We claim:

1. A prosthetic spinal disc, comprising:
   a biocompatible annulus comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (iii) will be located; and
   a nucleus within said biocompatible annulus, wherein said nucleus comprises a second material density, wherein an outer portion of said spinal disc comprises at least one pore to allow ingrowth of biological material, wherein said outer portion is selected from a group consisting of said first outer portion and said second outer portion, wherein said at least one pore comprises a plurality of pores formed at an angle with respect to said outer portion, wherein said plurality of pores are each formed at about 30 degrees in a spiral pattern.

2. A prosthetic spinal disc, comprising:
   a biocompatible annulus comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (iii) will be located;
   a nucleus within said biocompatible annulus, wherein said nucleus comprises a second material density; and
   at least one fiber optic passing through said annulus and terminating at an outer portion of said annulus selected from a group consisting of said first outer portion and said second outer portion.

3. The prosthetic spinal disc of claim 2, wherein said at least one fiber optic comprises a plurality of fiber optics.

4. The prosthetic spinal disc of claim 3, wherein said plurality of fiber optics pass through said annulus and said nucleus.

5. The prosthetic spinal disc of claim 3, further comprising means for providing electromagnetic radiation into said at least one fiber optic, wherein said electromagnetic radiation comprises a wavelength that causes ingrowth of beneficial tissues and cells.

6. The prosthetic spinal disc of claim 5, wherein said means for providing electromagnetic radiation comprise a laser.

7. The prosthetic spinal disc of claim 6, wherein said laser comprises a pulsed HO:YAG laser at a wavelength of about 2.09 $\mu$m, with a pulse duration of about 300 $\mu$s, a pulse repetition rate of about 5 Hz and a pulse energy within a range from 0.005 Joules to 0.08 Joules.

8. The prosthetic spinal disc of claim 6, wherein said laser comprises a continuous wave Erbium fiber laser at a wavelength of 1.56 $\mu$m and a power of from 1.5 to 3.0 watts.

9. A prosthetic spinal disc, comprising:
   a biocompatible annulus comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (iii) will be located; and
   a nucleus within said biocompatible annulus, wherein said nucleus comprises a second material density, wherein said nucleus comprises septae for dividing and strengthening said nucleus.

10. A prosthetic spinal disc, comprising:
    a biocompatible annulus comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (iii) will be located; and a nucleus within said biocompatible annulus, wherein said nucleus comprises a second material density, wherein an outer portion of said spinal disc comprises at least one pore to allow ingrowth of biological material wherein said outer portion is selected from a group consisting of said first outer portion and said second outer portion, wherein said at least one pore comprises a growth factor.

11. A prosthetic spinal disc, comprising:

a biocompatible annulus comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (iii) will be located; and a nucleus within said biocompatible annulus, wherein said nucleus comprises a second material density, wherein said biocompartible annulus comprises a material selected from a group consisting of polypropylene, polyethylene, polytretrafluoroethylene, polyurethane and polydinethylsiloxane.

12. A method of making a prosthetic spinal disc, comprising:

forming a biocompatible annulus from material comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (iii) will be located;

forming a nucleus within said biocompatible annulus, wherein said nucleus comprises a material having a second material density; and obtaining values for contouring said first outer portion and said second outer portion, wherein said values are obtained with a machine selected from a group consisting of a magnetic resonance imaging machine, a computed tomography machine and an ultrasound imaging machine.

13. A method of making a prosthetic spinal disc, comprising:

forming a biocompatible annulus from material comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (iii) will be located;

forming at least one pore in said outer portion to allow ingrowth of biological material, wherein said outer portion is selected from a group consisting of said first outer portion and said second outer portion, wherein said at least one pore comprises a plurality of pores formed at an angle with respect to said outer portion; and forming a nucleus within said biocompatible annulus, wherein said nucleus comprises a material having a second material density, wherein said plurality of pores are each formed at about 30 degrees in a spiral pattern.

14. A method of making a prosthetic spinal disc, comprising:

forming a biocompatible annulus from material comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (iii) will be located;

forming a nucleus within said biocompatible annulus, wherein said nucleus comprises a material having a second material density; and providing at least one fiber optic passing through said annulus and terminating at an outer portion of said annulus selected from a group consisting of said first outer portion and said second outer portion.

15. The method of claim 14, wherein said at least one fiber optic comprises a plurality of fiber optics.

16. The method of claim 15, wherein said plurality of fiber optics pass through said annulus and said nucleus.

17. A method of making a prosthetic spinal disc, comprising:

forming a biocompatible annulus from material comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (iii) will be located;

forming a nucleus within said biocompatible annulus, wherein said nucleus comprises a material having a second material density; and forming septae in said nucleus for dividing and strengthening said nucleus.

18. A method of making a prosthetic spinal disc, comprising:

forming a biocompatible annulus from material comprising a first material density, wherein said biocompatible annulus comprises (i) a first outer portion, (ii) a second outer portion and (iii) at least one lip, wherein at least one of said (i), (ii) or (iii) are contoured to substantially correspond to a surface of a vertebrae prior to placement against said vertebra against which at least one of said (i), (ii) or (ii) will be located;

forming at least one pore in said outer portion to allow ingrowth of biological material, wherein said outer portion is selected from a group consisting of said first outer portion and said second outer portion; and forming a nucleus within said biocompatible annulus, wherein said nucleus comprises a material having a second material density, wherein said at least one pore comprises a growth factor.

* * * * *